United States Patent [19]

Williams

[11] Patent Number: 5,047,583

[45] Date of Patent: Sep. 10, 1991

[54] PRODUCTION OF CARBOXYLIC ACIDS

[75] Inventor: Peter S. Williams, Hull, England

[73] Assignee: BP Chemicals Limited, London, England

[21] Appl. No.: 630,656

[22] Filed: Jul. 13, 1984

[30] Foreign Application Priority Data

Jul. 15, 1983 [GB] United Kingdom ................. 8319184

[51] Int. Cl.$^5$ ................. C07C 51/353; C07C 53/122; C07C 53/08
[52] U.S. Cl. ................. 562/606; 260/405.6; 560/234; 562/607; 562/609
[58] Field of Search ................. 562/606, 517, 607; 260/405.6, 413

[56] References Cited

U.S. PATENT DOCUMENTS 3,772,380 11/1973 Paulik et al. ................. 560/232
3,839,428 10/1974 Isogai ................. 562/517 X
4,100,359 7/1978 Schmerling et al. ................. 562/232

FOREIGN PATENT DOCUMENTS 0045637 2/1982 European Pat. Off. .
0060695 9/1982 European Pat. Off. .
1286224 8/1972 United Kingdom .

OTHER PUBLICATIONS

Mizorogi, Shokubai, 19, No. 2, pp. 90–95 (1977).

Primary Examiner—Vivian Garner
Attorney, Agent, or Firm—Brooks Haidt Haffner & Delahunty

[57] ABSTRACT

A carboxylic acid of formula $RCO_2H$, for example acetic acid, is prepared from a formate ester of formula $HCO_2R$, for example methyl formate, by heating the ester at elevated temperature with an iridium catalyst, a halide promoter and a strong acid. The strong acid is one having a pKa of not greater than 0 in aqueous media for example a sulphonic acid. Addition of the strong acid to the reaction mixture causes an increase in the rate of conversion of formate ester to carboxylic acid.

22 Claims, No Drawings

PRODUCTION OF CARBOXYLIC ACIDS

This invention relates to a process for the preparation of carboxylic acids more particularly to the preparation of aliphatic carboxylic acids by the isomerisation of esters of formic acid.

The conversion of esters of formic acid to the corresponding carboxylic acid in the presence of carbon monoxide and a Group VIII metal catalyst has been previously described in U.S. Pat. No. 3,839,428 and GB Pat. No. 1,286,224 discloses a process for the preparation of acetic acid by heating methyl formate in the presence of carbon monoxide, a rhodium catalyst and a halogen promoter.

European Patent Application No. 045637 has disclosed that the isomerisation reaction, when operated using an iodide promoted iridium catalyst, has the advantage over the rhodium catalysed reaction that carbon monoxide is not required to maintain catalyst efficiency. However, a disadvantage of the iridium catalyst system is that the reaction rate is lower than that obtained when using rhodium.

It has now been found that the reaction rate of the iridium catalysed isomerisation reaction can be improved by incorporating a strong acid into the reaction.

Accordingly, the present invention comprises a process for the preparation of a carboxylic acid of formula $RCO_2H$ from an ester of formic acid of formula $HCO_2R$, where R is a $C_1$ to $C_{10}$ aliphatic hydrocarbyl group, which process comprises reacting the formic acid ester at elevated temperature and superatmospheric pressure with an iridium catalyst and a halide promoter characterised in that the reaction is carried out in the presence of a strong acid.

The halide promoter can be added as free halogen, as the hydrogen halide, or as RX where R is as defined above particularly methyl or ethyl. The halide promoter is preferably an iodide.

The iridium can be added in the form of the metal or a salt or complex such as $[Ir(cyclooctadiene)Cl]_2$, $Na_2IrCl_6 \cdot XH_2O$, $HIrCO[P(C_6H_5)_3]_3$, $ClIrCO(PEt_3)_2$, $IrCl_3 \cdot XH_2O$, $IrI_3 \cdot XH_2O$, $Na_3Ir(NO_2)_6 \cdot XH_2O$, $K_3Ir(CN)_6$, $[(C_5H_5)_2Ir]NO_3$, $Ir_4(CO)_{12}$, $IrH_3[P(C_6H_5)_3]_3$, $1,2,3$-$py_3IrCl_3$, $trans[Irpy_4Cl_2]Cl$ and $(C_8H_{12})_2IrSnCl_3$. Preferred salts are $[Ir(cyclooctadiene)Cl]_2$, $IrCl_3 \cdot XH_2O$, $IrBr_3 \cdot XH_2O$ and $IrI_3 \cdot XH_2O$. The symbol X indicates differing degrees of hydration and varies from 0 to 12.

By strong acid is meant an acid having a pKa of not greater than 0 measured in an aqueous medium. The strong acid can be a sulphonic acid or the like, for example sulphonic acid such as p-toluene sulphonic acid, methane sulphonic acid and the like. The strong acid may be soluble in the reaction medium but can also be a supported or polymeric sulphonic acid which is insoluble therein. Use of an insoluble sulphonic acid considerably simplifies separation of the strong acid from the product mixture.

Concentrations in excess of 10% by weight of strong acid based on the total reaction mixture including solvent if present can be employed, although in practice concentrations in the range 1.5 to 10% by weight are the most convenient.

In the case of a sulphonic acid the molar ratio of sulphonic acid to iridium is conveniently at least 10:1. Whilst there is no upper limit it is preferred that the ratio is from 10:1 to 150:1.

The isomerisation reaction is conveniently carried out at elevated temperature and superatmospheric pressure. The temperature of reaction is conveniently in the range 100° to 300° C. and preferably in the range 150° to 250° C. As regards pressure, this can be generated by the autogenous vapour pressure of the reactants at the temperature of reaction although it is preferable to add a further overpressure of a gas to increase the pressure further. The gas can be carbon monoxide or an inert gas such as nitrogen, hydrogen, helium, argon or the like, but is preferably a gas in which oxygen is substantially absent. In any event, the reaction is effected at a pressure in the range 200 to 1200 psig, preferably 200–800 psig.

The ester of formic acid of formula $HCO_2R$ can be added as such or can be formed in situ from its precursors. Thus, for example methyl formate can be formed from formic acid and a methyl carboxylate such as methyl acetate, methyl propionate or methyl butyrate.

It is preferable that the reactants and products are maintained in the liquid phase and that the catalyst is present therein. To achieve this a solvent may be added to the reactor. Suitable solvents are monocarboxylic acids having from 2 to 11 carbon atoms e.g. acetic acid, propionic acid, hexanoic acid, decanoic acid and the like. The carboxylic acid produced by the isomerisation reaction can itself be used as the solvent for further reaction.

Although it is preferable to carry out the reaction in the liquid phase, the invention described herein also contemplates embodiments in which the reaction is effected in the gas or vapour phase with the catalyst system present as a solid.

The reaction can be effected batchwise or continuously.

The invention is illustrated by the following examples in which the catalyst was employed in solution.

Example 1

To a corrosion resistant autoclave of capacity 100 mls was charged 35.7 g methyl formate, 5.5 g methyl iodide, 4.1 g p-toluene sulphonic acid and 0.1 g iridium trichloride. The autoclave was flushed several times with nitrogen and then pressurised with nitrogen to 300 psig. The reactor was then heated to 200° C. and this temperature was maintained for 1 hr, during which time the pressure in the reactor did not exceed 600 psig. After 1 hr, the autoclave was cooled and depressurised, and the product recovered and analysed by gas chromatography (GC). It was found to contain by weight of total mixture 61.8% acetic acid and 14.9% methyl acetate. The latter as formed from the transesterification between methyl formate and acetic acid.

Example 2

To the reactor of Example 1 was charged 35.0 g methyl formate, 5.6 g methyl iodide, 2.0 g p-toluene sulphonic acid and 0.1 g iridium trichloride. The procedure described in Example 1 was then followed, except that the reaction time at 200° C. was 0.8 hours. The product was found to contain by weight of total mixture 9.35% acetic acid and 20.1% methyl acetate.

Example 3

To the reactor of Example 1 was charged 40.0 g ethyl formate, 4.7 g ethyl iodide, 3.0 g methane sulphonic acid and 0.1 g iridium trichloride. The autoclave was flushed with nitrogen, then charged with 300 psig nitrogen, and then heated to 200° C. for 6 hours. The product recovered after cooling was analysed by Gc and found to contain by weight of the total mixture 36.0% propionic acid and ca. 31% ethyl propionate.

Example 4

To the autoclave of Example 1 was charged 35.0 g methyl formate, 4.9 g methyl iodide, 4.0 g p-toluene sulphonic acid and 0.1 g iridium trichloride. The reactor was then sealed, flushed with nitrogen and then pressurised with 300 psig nitrogen. The pressurised reactor was then heated to 175° C. for 1 hr. After 1 hr, the reactor was cooled, and the product found to contain by wt of total mixture 3.2% acetic acid and 13.7% methyl acetate.

Example 5

The autoclave of Example 1 was charged with 20.0 g propionic acid, 20.0 g methyl formate, 4.0 g p-toluene sulphonic acid, 5.0 g methyl iodide and 0.1 g iridium trichloride. The procedure of Example 1 was then followed. The product was found to contain by weight of total mixture 31.65% acetic acid and 5.0% methyl acetate.

Comparative Experiment A

The autoclave of Example 1 was charged with 35.0 g methyl formate, 5.3 g methyl iodide, and 0.103 g iridium trichloride. The procedure of Example 1 was then followed. Analysis of the product by G.C. showed it to contain by weight of total mixture only c.a. 0.1% methyl acetate and 0.1% acetic acid.

This experiment when compared with Example 1 demonstrates that the conversion in the absence of a strong acid is much lower.

Example 6

To the autoclave of Example 1 was charged 35.0 g methyl formate, 5.2 g methyl iodide, 4.0 g methane sulphonic acid, and 0.103 g iridium trichloride. The autoclave was then sealed, flushed several times with carbon monoxide, pressurised to 500 psig with carbon monoxide, and then heated to 200° C. for a period of one hour. During this time the pressure reached a maximum of 1040 psig. Upon cooling, the pressure returned to 500 psig. GC. analysis of the liquid product showed it to contain by weight of total mixture 64% acetic acid and 4.8% methyl acetate.

Example 7

To the autoclave of Example 1 was charged 25.2 g of methyl formate, 20.0 g of propionic acid (solvent), 5.8 g of mehtyl iodide 4.2 g of methane sulphonic acid and 0.101 g of iridium trichloride. The autoclave was flushed with nitrogen and pressurised to 500 psig with nitrogen. The autoclave was then heated to 200° C. and this temperature was maintained for approximately 15 mins. After cooling the contents of the autoclave were removed and analysed by Gc. The product contained by wt of total mixture 23.3% of acetic acid and 8.3% methyl acetate. This corresponds to a productivity in excess of 10 moles of product acetates/litre liquid charge/hour.

Comparative Experiment B

The procedure of Example 7 was followed except that the methane sulphonic acid was omitted and the weights of the other compounds charged to the autoclave were as follows:

24.9 g methyl formate
24.1 g propionic acid
5.8 g methyl iodide
0.108 g iridium trichloride.

The product was found to contain only 1.1% acetic acid and 0.4% methyl acetate by wt of the total mixture. This comparative experiment when compared with Example 7 shows the benefit of adding sulphonic acid in the presence of a carboxylic acid solvent. The advantages of the above described iridium catalysed reaction effected in the presence of strong acid are:

(i) the reaction rate is greater than that disclosed in EP 045637 which describes the reaction effected in the absence of strong acid,
(ii) a carboxylic acid is not required to be present at the start of the reaction as disclosed in EP 045637,
(iii) as compared with prior art catalyst systems containing rhodium, the iridium-containing catalyst does not require the presence of carbon monoxide to maintain activity.

I claim:

1. In a process for the preparation of a carboxylic acid of the formula $RCO_2H$ from an ester of formic acid of the formula $HCO_2R$, where R is a $C_1$ to $C_{10}$ aliphatic hydrocarbyl radical, which process comprises reacting the formic acid ester at elevated temperature and superatmospheric pressure with a halide promoter and an iridium catalyst selected from the group consisting of $[Ir(Cyclooctadiene)Cl]_2$, $HIrCO[P(C_6H_5)_3]_3$, $Na_2IrCl_6 \cdot XH_2O$, $ClIrCO(PEt_3)_2$, $UrBr_3 \cdot XH_2$), $IrCl_3 \cdot XH_2O$, $IrI_3 \cdot XH_2O$, $Na_3IrNO_2O$, $[(C_5H_5)_2Ir]NO_3$, $Ir_4(CO)_{12}$, $IrH_3[P(C_6H_5)_3]_3$, 1,2,3-py$_3$IrCl$_3$, trans[Ir py$_4$Cl$_2$]Cl, $(C_8H_{12})_2$IrSnClhd 3, and iridium metal, where X indicates differing degrees of hydration and varies from 0 to 12, the improvement which comprises carrying out the reaction in the presence of a strong acid comprising a sulphonic acid.

2. A process as claimed in claim 1 wherein the reaction is effected in the absence of carbon monoxide.

3. A process as claimed in claim 1 wherein the reaction is carried out in the presence of carbon- monoxide.

4. A process as claimed in claim 1 wherein the reaction is effected in the substantial absence of oxygen.

5. A process as claimed in claim 1 wherein the ester of formic acid is methyl formate and the carboxylic acid is acetic acid.

6. A process as claimed in claim 1 wherein the reactants and products are maintained in the liquid phase and the catalyst is present therein.

7. A process as claimed in claim 1 wherein a carboxylic acid solvent is employed.

8. A process as claimed in claim 7 wherein the carboxylic acid solvent is the carboxylic acid of formula $RCO_2H$ produced during the reaction.

9. A process as claimed in claim 1 wherein the sulphonic acid is p-toluene sulphonic acid.

10. A process as claimed in claim 1 wherein the sulphonic acid is methane sulphonic acid.

11. A process as claimed in claim 1 wherein the sulphonic acid is a polymeric sulphonic acid.

12. A process as claimed in claim 2 wherein the sulphonic acid is present in excess of 10% by weight based on the total reaction mixture.

13. A process as claimed in claim 1 wherein the sulphonic acid is present in the range of 1.5 to 10% by weight based on the total reaction mixture.

14. A process as claimed in claim 1 wherein the molar ratio of sulphonic acid to iridium is at least 10:1.

15. A process as claimed in claim 1 wherein the molar ratio of sulphonic acid to iridium is from 10:1 to 150:1.

16. A process as claimed in claim 1 wherein the elevated temperature is in the range of 100 to 300° C.

17. A process as claimed in claim 1, wherein the elevated temperature is in the range of 150° to 250° C.

18. A process as claimed in claim 1 wherein the superatmospheric pressure is in the range of 200 to 1200 psig.

19. A process as claimed in claim 1 wherein the superatmospheric pressure is in the range of 200 to 800 psig.

20. A process as claimed in claim 1 wherein the reaction is carried out in the presence of an inert gas selected from the group consisting of nitrogen, hydrogen, helium and argon.

21. A process as claimed in claim 1 wherein the sulphonic acid is selected from the group consisting of p-toluene sulphonic acid and methane sulphonic acid.

22. A process as claimed in claim 1 wherein the ester of formic acid is ethyl formate and the carboxylic acid is propionic acid.

* * * * *

UNITED STATES PATENT AND TRADEMARK OFFICE
CERTIFICATE OF CORRECTION

PATENT NO. : 5,047,583
DATED : September 10, 1991
INVENTOR(S) : PETER S. WILLIAMS It is certified that error appears in the above-identified patent and that said Letters Patent is hereby corrected as shown below:

Col. 2, l. 15, the formula should read "$HCO_2R$"

Col. 2, l. 37, should read --in which the reactants and products were maintained in the liquid phase and the catalyst was employed in solution.--

Col. 3, l. 2 and 60, correct the abbreviation to "GC"

Col. 4, l. 11, "The advantages of" should start a new paragraph
Column 4:

Claim 1, lines 8-12, should read

--[Ir (Cyclooctadiene)Cl]$_2$, HIrCO[P(C$_6$H$_5$)$_3$]$_3$, Na$_2$IrCl$_6$·XH$_2$O, ClIrCO(PEt$_3$)$_2$, IrCL$_3$·XH$_2$O, IrBr$_3$·XH$_2$O, IrI$_3$·XH$_2$O, Na$_3$Ir(NO$_2$)$_6$·XH$_2$O, [(C$_5$H$_5$)$_2$Ir]NO$_3$, Ir$_4$(CO)$_{12}$, IrH$_3$[P(C$_6$H$_5$)$_3$]$_3$, 1,2,3-py$_3$IrCl$_3$, trans[Ir py$_4$Cl$_2$]Cl, (C$_8$H$_{12}$)$_2$IrSnCl$_3$, and iridium metal.--

Signed and Sealed this

Second Day of March, 1993

*Attest:*

STEPHEN G. KUNIN

*Attesting Officer*   *Acting Commissioner of Patents and Trademarks*